US00PP36826P2

(12) United States Plant Patent
Hansen

(10) Patent No.: US PP36,826 P2
(45) Date of Patent: Jul. 15, 2025

(54) ***VERONICA* PLANT NAMED 'Da Vinci Delight'**

(50) Latin Name: *Veronica spicata*
Varietal Denomination: Da Vinci Delight

(71) Applicant: Hans A. Hansen, Zeeland, MI (US)

(72) Inventor: Hans A. Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 18/831,468

(22) Filed: Jan. 29, 2025

(51) Int. Cl.
*A01H 5/02* (2018.01)
*A01H 6/68* (2018.01)

(52) U.S. Cl.
USPC ..... Plt./251
CPC ..... *A01H 6/68* (2018.05)

(58) Field of Classification Search
USPC ..... Plt./251
CPC ..... A01H 5/02
See application file for complete search history.

*Primary Examiner* — Kent L Bell

(57) ABSTRACT

A new and distinct cultivar of ornamental Spiked Speedwell, *Veronica spicata* plant named 'Da Vinci Delight', with broad medium-height habit, stiff, upright, compound-branched spikes of densely-arranged soft lilac flowers beginning in early summer and continuing for at least six weeks above dark-green, lanceolate, highly lustrous foliage. The new plant is useful in the landscape as a specimen, en masse, as a container plant, or as a cut flower, and maintains its foliage through the season.

2 Drawing Sheets

Botanical classification: *Veronica spicata.*
Variety denomination: 'Da Vinci Delight'.

STATEMENT REGARDING PRIOR DISCLOSURES UNDER 37 CFR 1.77(b)(6)

The newly claimed plant was first offered for sale on a website operated by Walters Gardens, Inc. on Feb. 1, 2024. Subsequently, on May 23, 2024, the new plant was described with a photograph in the "Walters Gardens 2024-2025 Catalog" by Walters Gardens, Inc. Walters Gardens, Inc. obtained the plant and all information relating thereto, from the inventor. No plants of *Veronica* 'Da Vinci Delight' have been sold or offered for sale in this country or anywhere in the world, nor has any disclosure of the new plant been made more than one year prior to the filing date of this application and such sale or disclosure within one year was either derived directly or indirectly from the inventor and would be a 35 U.S.C § 102b exception.

BACKGROUND OF THE INVENTION

The present invention relates to the new and distinct cultivar of Spiked Speedwell, botanically known as *Veronica* 'Da Vinci Delight', and hereinafter referred to as the cultivar 'Da Vinci Delight' or the "new plant". The new plant was selected as an individual seedling from a cross by the inventor on Jun. 27, 2016, performed by the inventor in the hybridizing greenhouses of a wholesale perennial nursery in Zeeland, Michigan, USA between 'Very Van Gogh' U.S. Plant Pat. No. 27,482 as the female or seed parent and 'Royal Rembrandt' U.S. Plant Pat. No. 29,377 as the male or pollen parent.

The new plant was assigned the breeder code of 16-5-2. 'Da Vinci Delight' has been asexually propagated initially by division and later by basal cuttings and shoot tip tissue culture at the same nursery in the greenhouses in Zeeland, MI, since the summer of 2018 with subsequent asexually propagated plants found to be identical to the original selection with all the same traits as the original seedling though multiple generations.

BRIEF SUMMARY OF THE PLANT

*Veronica* 'Da Vinci Delight' is unique from all other Spiked Speedwell known to the inventor. Several other cultivars may have some similar traits, but this is the only variety known by the inventor to have the following characteristic combinations that establish the new plant as unique:

1. Compact, medium height with stiff, upright spikes above dense stems of dark-green foliage;
2. Flowering in numerous spikes with densely-arranged soft lilac flowers;
3. Dark-green, highly lustrous, lanceolate foliage;
4. Compound-branched spikes begin blooming in early summer and continue for at least six weeks into early autumn;
5. Maintains foliage through the season with good disease resistance.

The closest comparison varieties known to the inventor are 'Lavender Lightsaber' U.S. Plant Pat. No. 32,359, 'Atomic Lilac' U.S. Plant Pat. No. 21,867, 'Hocus Pocus' U.S. Plant Pat. No. 23,853, 'Purple Leia' U.S. Plant Pat. No. 34,278, and 'Amethyst Plume' U.S. Plant Pat. No. 24,411.

'Lavender Lightsaber' is taller and narrower in habit and has a flower color that is a lighter rosy purple. 'Atomic Lilac' has a slightly shorter less dense habit, the peduncles are less branched, and the flowers are of a slightly different hue on shorter peduncles. 'Hocus Pocus' has a narrower habit and the flowers are a violet-purple. 'Purple Leia' is about 50 percent taller, with a shorter flowering season, and the flowers are on longer spikes with longer branches. 'Amethyst Plume' has flowers that are deep purple-pink with peduncles that are branched nearer the apex, and the habit is taller and narrower than the new plant.

'Very Van Gogh' has a narrower habit and flowers that are a deeper rosy-purple on shorter peduncles. 'Royal Rembrandt' has a narrower habit and flowers that are violet-purple on less branched peduncles.

BRIEF DESCRIPTION OF THE DRAWINGS

The photographs of the new plant demonstrate the overall appearance and unique traits of 'Da Vinci Delight' as two-year-old plants grown in a full-sun display garden in Zeeland, Michigan. The colors are as accurate as reasonably possible with color reproductions. Variation in ambient light spectrum, source and direction may cause the appearance of minor variation in color.

DETAILED BOTANICAL DESCRIPTION

Figure 1:
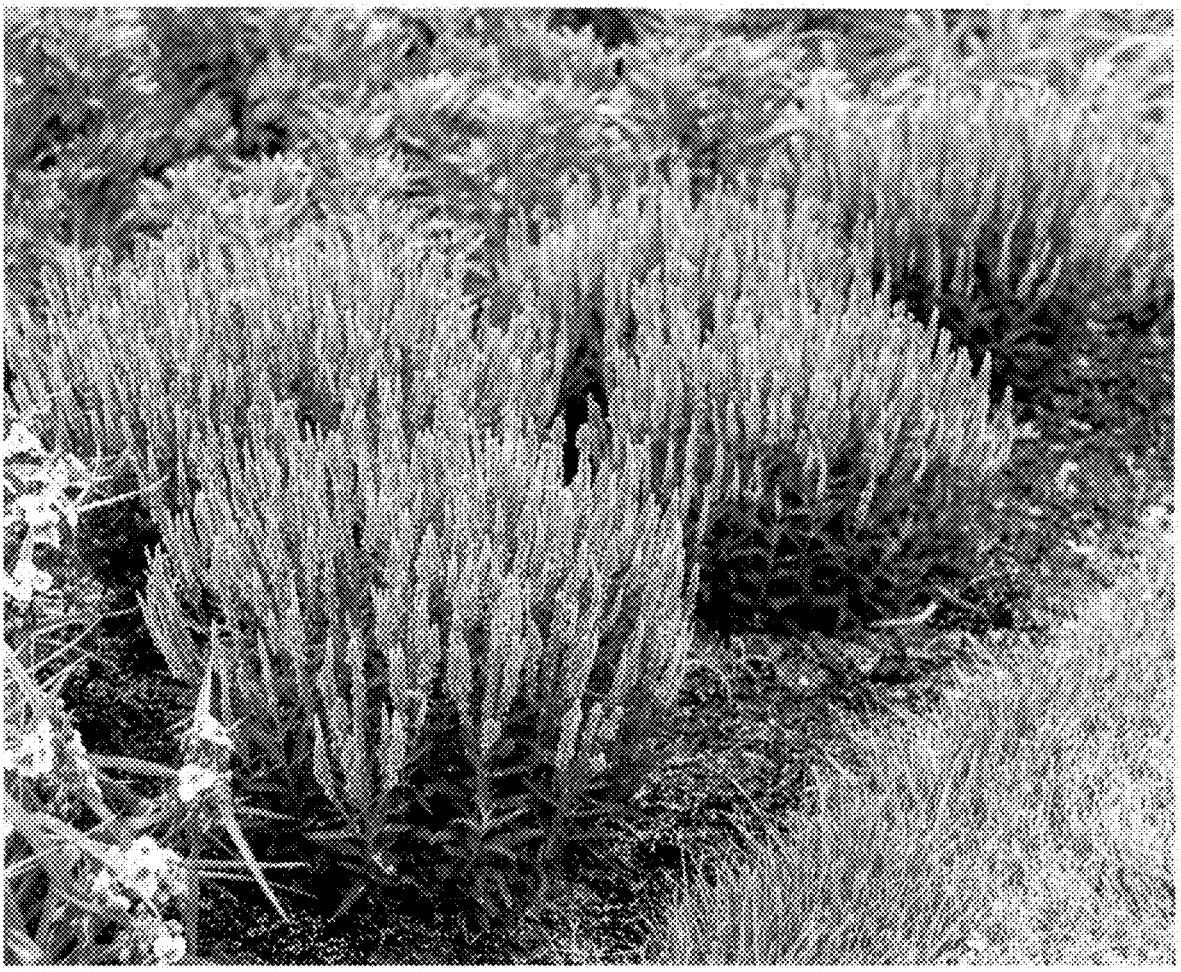
FIG. 1 shows a row of the new plants in early full flower.
Figure 2:
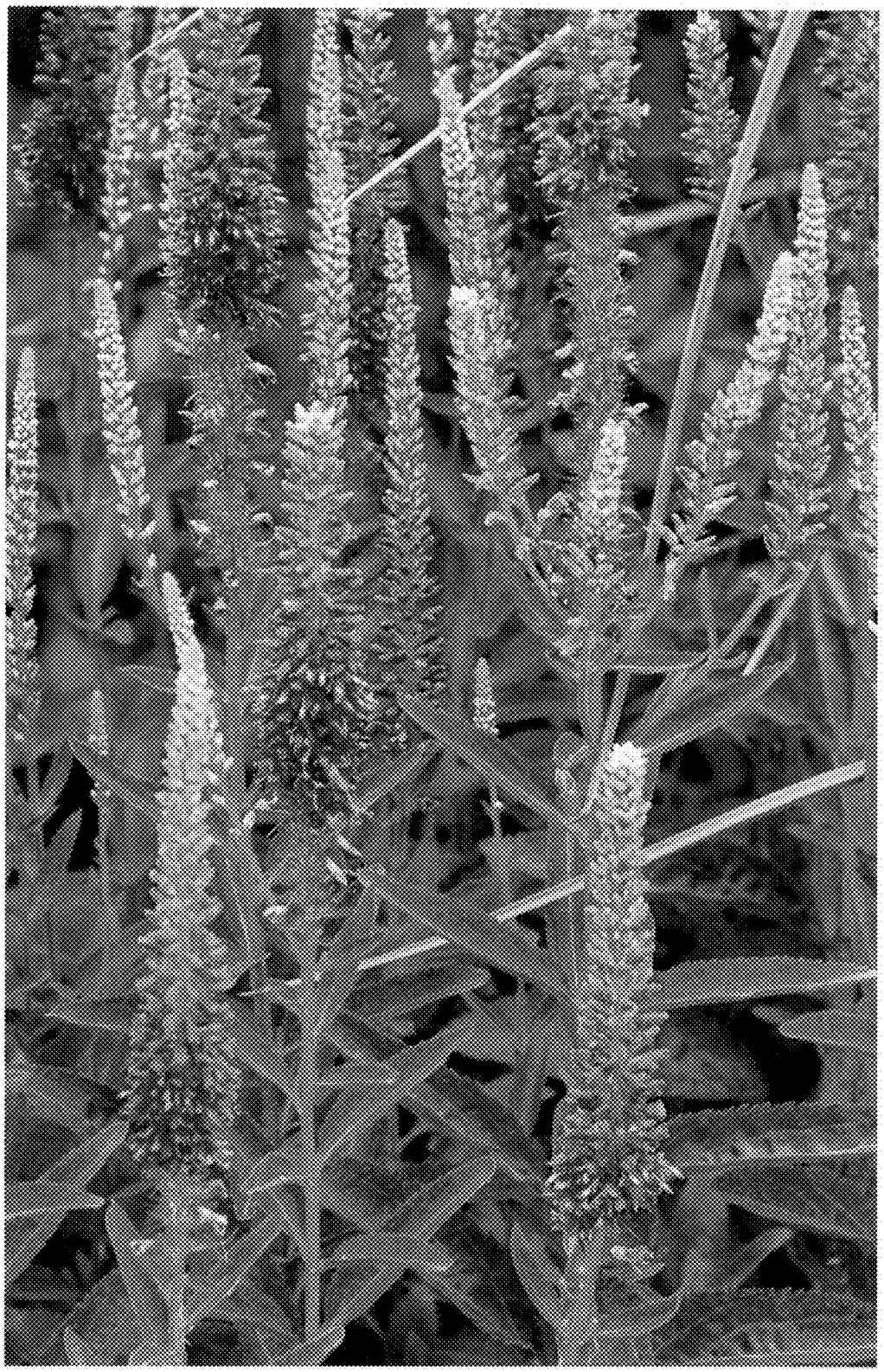
FIG. 2 shows a close-up of the flowers and buds.

The following descriptions and color references of *Veronica* 'Da Vinci Delight' are based on the 2015 edition of The Royal Horticultural Society Colour Chart except where common dictionary terms are used. 'Da Vinci Delight' has not been observed under all possible environments. The phenotype may vary slightly with different growing environments such as temperature, light, fertility, soil pH, moisture and maturity levels, but without any change in the genotype. The following observations and descriptions are based on two-year-old plants grown in a full-sun display garden of a wholesale perennial nursery in Zeeland, Michigan.

Botanical classification: *Veronica spicata;*

Parentage: The female parent is 'Very Van Gogh', the male parent is 'Royal Rembrandt';

Propagation: The plant roots from cuttings in about 2 weeks and flowers in a 3.8-liter container in 8 to 10 weeks following an optimal vernalization period of about 8 weeks;

Roots: Fibrous; heavily branching; color between RHS 164C and RHS 164D;

Plant habit: Hardy herbaceous perennial, compact, with about 72 stems; main stems branching in distal portion; to about 55 cm tall and clumping to about 66 cm wide; flowering beginning early summer in Michigan and continuing for at least six weeks;

Leaves: Simple; flat; lanceolate; opposite; acute apex; distal leaves with attenuate base and proximal leaves with rounded to cuneate base; margin serrate, serrated with about 4 teeth per centimeter; teeth to about 1.5 mm long; adaxial micro-puberulent and glabrous abaxial, highly lustrous adaxial and matte abaxial;

Leaf size: To about 95 mm long by 25 mm wide near the middle, average about 85 mm long and 20 mm wide, decreasing distally in both length and width; about 16 leaves per stem;

Leaf color: Mature adaxial between RHS NN137A and RHS 136A, abaxial between RHS 137A and RHS 147A; young expanding adaxial nearest RHS 137B, abaxial nearest RHS 146B;

Veins: Pinnate; adaxial glabrous and flat; abaxial glabrous and flat, abaxial midrib costate;

Vein color: Adaxial midrib and proximal lateral veins between RHS 147C and RHS 146D distal lateral veins nearest RHS 146C; abaxial midrib nearest RHS 146C distally and nearest RHS 146D proximally and lateral veins nearest RHS 137B;

Petiole: Simple; glabrous abaxial and adaxial; margin micro-ciliolate; base slightly clasping; to about 10 mm long and 4 mm wide decreasing distally to an average about 6.5 mm long and 3 mm wide;

Petiole color: Adaxial between RHS 138B and RHS 146C; abaxial nearest RHS 138A;

Stem: Cylindrical; puberulent; stiff; upright; length about 20 to 26 cm before flowers, diameter about 5 mm at base; color nearest RHS 146D;

Internodes: Typically, 7 below flowers; average about 2.5 cm apart; node color variable, nearest RHS 138A;

Inflorescence: Compound branched upright spikes in compressed conglomerate; to about 30 cm long and 11 cm wide with 8 lateral branches; the plant continues to flower adding to the terminal end of the main stem and branches, with about 200 flowers per center stem, 80 flowers per primary branch and about 400 to 800 flowers per branched peduncle; branches upright; to about 27 cm long and 2 mm diameter at base;

Flower bud one to two days prior to opening: Convolute, oblong; rounded base and acute apex; glabrous; about 6 mm long and 1.5 mm diameter;

Flower bud color one to two days prior to opening: Nearest RHS N82A;

Flowers: Zygomorphic; perfect; complete; about 6 mm wide and about 9 mm long to exserted anthers; corolla about 6 mm across, 6 mm tall, and about 6 mm long; corolla tube fused in basal 3 mm, and 2 mm diameter near base; flowers persist individually for 4 to 6 days on the plant or as cut flower; petals self-cleaning, sepals and style persistent;

Flower aspect: Outwardly;

Flower fragrance: None detected;

Flower timing: Early summer and continuing for at least six weeks;

Petals: Four, rarely 3, five, or six; one slightly larger dorsal petal above, two lateral, one ventral slightly smaller below; acute apices; entire; glabrous adaxial and abaxial except basal 2 mm adaxial of fused tube with pubescent tuft; fused in basal 3 mm; larger dorsal petal 3 mm wide and 6 mm long, lateral side petals about 6 mm long by 2 mm wide, ventral petal about 6 mm long and 2 mm wide;

Petal color: Abaxial and adaxial nearest RHS N81B with corolla tube base lightening RHS NN155D with proximal 0.5 mm nearest RHS 145D; adaxial tuft of hairs nearest RHS NN155D;

Androecium:

*Filaments*.—Two, rarely three; divergent; cylindrical; glabrous; epipetalous about 1 mm from base; about 8 mm long by 0.3 mm diameter; color nearest RHS N81C distally and in the proximal two mm nearest RHS NN155C.

*Anther*.—Dorsifixed, longitudinal; ellipsoidal; with rounded ends; about 2 mm long and 1 mm wide; color adaxial nearest RHS 181D abaxial nearest RHS N81A.

*Pollen*.—Abundant, globose, less than 0.1 mm; color nearest RHS 8C.

Gynoecium: One, superior; exserted; persists after petal drop; to about 9 mm long;

*Style*.—Cylindrical; straight; aspect outwardly to slightly drooping; to about 8 mm long by 0.3 mm; color nearest RHS N81C proximally and nearest RHS N81B distally.

*Stigma*.—Globose; about 0.2 mm in diameter; color nearest RHS N81B.

*Ovary*.—Ellipsoid; about 1 mm long and 0.7 mm across; color nearest RHS 145A.

Calyx: Campanulate; 4 mm long, 4 mm across and 4 mm tall;

Sepals: Typically, four; two larger and two smaller; lanceolate; adaxial and abaxial dull and glabrous; acute apex; margin entire, micro-ciliolate; basal 1 mm fused and then flared forming a broad campanulate calyx; larger pair about 4 mm long and 1 mm wide; smaller pair about 4 mm long and 0.7 mm wide;

Sepal color: Abaxial and adaxial nearest RHS 137A;

Peduncle: About 72 per plant; raceme; strong; stiff but flexible; virgate; branched at upper two to four nodes; cylindrical; puberulent distally and at branches, to glabrescent proximally; flowering portion to about 27 cm long, about 11 cm across with branches;

Main peduncle, primary and secondary branches color: Nearest RHS 146D;

Branches: Cylindrical; puberulent; at about 30° angle from vertical and then erect in flowering portion; to about 25 cm long and 2 mm diameter;

Pedicel: Rigid; cylindrical, puberulent; about 0.5 mm long and 0.5 mm wide, aspect outwardly to slightly upwardly;

Pedicel color: Nearest RHS 138B;

Bract: Single; subtending each flower; linear; narrowly acute apex; entire; sessile truncate base; proximal bracts about 22 mm long and 6 mm wide and decreasing distally to about 3 mm long and less than 1 mm wide;

Bract color: Adaxial between RHS NN137A and RHS 139A, abaxial and nearest RHS NN137A;

Fruit: Not yet observed;

Growth: The new plant grows best with plenty of moisture and adequate drainage, but is able to tolerate some drought when mature.

Hardiness: Winter hardiness at least from USDA zone 4 through 8.

Disease and pest resistance and susceptibility beyond what is typical of that of other spiked speedwell has not been observed.

I claim:

1. A new and distinct cultivar of *Veronica* plant named 'Da Vinci Delight' as herein described and illustrated.

* * * * *